(12) United States Patent  
Wolter

(10) Patent No.: US 6,706,071 B1  
(45) Date of Patent: Mar. 16, 2004

(54) PROSTHETIC HIP JOINT ASSEMBLY

(76) Inventor: Dietmar Wolter, c/o Berufsgenossenschaftliches Unfallkrankenhaus, Bergedorfer Strasse 10, D-21033 Hamburg (DE)

( * ) Notice: Subject to any disclaimer, the term of this patent is extended or adjusted under 35 U.S.C. 154(b) by 0 days.

(21) Appl. No.: 09/578,198

(22) Filed: May 24, 2000

(51) Int. Cl.$^7$ .................................................. A61F 2/32
(52) U.S. Cl. .................................. 623/22.13; 623/22.17
(58) Field of Search ........................... 623/22.17, 22.13, 623/22.11, 22.15, 22.2, 22.26, 22.3, 22.4, 18.11, 19.12

(56) References Cited

U.S. PATENT DOCUMENTS

| | | | |
|---|---|---|---|
| 3,269,758 A | * | 8/1966 | Ulderup et al. |
| 3,683,421 A | * | 8/1972 | Martinie ........................ 623/22 |
| 3,864,758 A | * | 2/1975 | Yakich ........................ 623/22.4 |
| 4,731,088 A | * | 3/1988 | Collier ........................ 623/22 |
| 5,197,488 A | * | 3/1993 | Kovaceric ..................... 128/782 |
| 5,389,107 A | | 2/1995 | Nassar et al. .................. 623/23 |
| 5,514,182 A | | 5/1996 | Shea ............................ 623/18 |
| 5,702,474 A | | 12/1997 | McCandliss ................... 623/22 |
| 5,702,483 A | * | 12/1997 | Kwong .......................... 623/23 |
| 5,755,807 A | | 5/1998 | Anstaett et al. ................ 623/23 |
| 5,769,093 A | * | 6/1998 | Bays ........................... 128/898 |
| 6,432,141 B1 | * | 8/2002 | Stocks et al. .............. 623/22.13 |

FOREIGN PATENT DOCUMENTS

| | | |
|---|---|---|
| DE | 37 41 490 | 6/1989 |
| DE | 295 02 961 | 6/1995 |

* cited by examiner

Primary Examiner—Corrine McDermott
Assistant Examiner—Alvin Stewart
(74) Attorney, Agent, or Firm—Vidas, Arrett & Steinkraus, P.A.

(57) ABSTRACT

An artificial hip joint assembly comprising a femoral component with a stem for being anchored in the medullary space of a femur and a head on the distal end of the stem, an acetabular component for being anchored in the pelvic bone with an acetabular cup which pivotedly supports the head of the femoral component, and an articular capsule made of a flexible material, which is located at the femoral component at one end and at the acetabular component at the other end so as to allow the head to move in the acetabular cup and to prevent wear debris from the bearing zone of the head in the acetabular cup from migrating to the outside.

20 Claims, 2 Drawing Sheets

PROSTHETIC HIP JOINT ASSEMBLY

CROSS-REFERENCE TO RELATED APPLICATIONS

This Application claims benefit of German Appln. Number 19924676.9 filed on May 29, 1999.

STATEMENT REGARDING FEDERALLY SPONSORED RESEARCH

Not Applicable

BACKGROUND OF THE INVENTION

The invention relates to an endoprosthesis for the human hip joint. Artificial hip joint assemblies are used in surgery and orthopaedy when the hip joint proper has been destroyed because of diseases, wear or injuries and gives pain when in function.

As a rule, a resection is then made on the destroyed joint portions and an artificial hip joint assembly is implanted. This hip joint assembly, as a rule, is made of plastic and metallic components. The plastic material, as a rule, is polyethylene whereas the metals are forged steels and, especially, titanium alloys.

Whenever the artificial hip joint assembly is moved in the body fine wear debris particles will form. These fine particles are released to the surrounding tissue. The body will then make efforts to neutralize and carry away these microparticles. This is done by foreign matter transporting giant cells. Transport is then effected into the remaining organism via the lymphatic vessel system.

The isolation and neutralization of such microparticles leads to significant alterations to the tissue. An osteolysis might occur, i.e. a loss of the periprosthetic bone portions of the prosthetic assembly. Nowadays, this alteration to the tissue in the adjoining bone by wear debris particles is considered an important cause of the loosening of endoprostheses. Grave alterations to the bone will then be recognized after a period of 10 to 20 years.

Attempts have been made already to reduce the generation of the microparticles with a view to increasing the stability in operation of the prosthetic assemblies.

A substantial improvement to joint functionality was achieved in decades of research work through an optimization of the pairs of sliding elements. Thus, for example, ceramic materials were introduced into endoprosthetics as mating elements that slide. In addition, progress was made particularly in the cementless implantation of prostetic hip joint assemblies. At this point, an important progress is the fact that a firm inlay in titanium or a titanium alloy is introduced in the region of the acetabular cup by locking it in the bony cup. A snugly fitting clamshell-shaped insert in polyethylene will then be placed in this artificial acetabular cup. Fixation of the artificial hip joint in the thigh region is effected by means of a stem which is inserted in the medullary space of the femur. A spherically shaped head is fixed on the end of the prosthetic stem by means of a cone fit.

In addition, the head may include a neck-type shape which has a conical seat to receive a cone of the prosthetic stem with different neck lengths being available. As a rule, the head is made of steel or a ceramic material.

When the artificial hip joint is operative a motion of the head is caused in the acetabular cup. Studies have shown that very fine debris particles may form whenever a step is made.

The acetabular cup or the insert will then undergo thinning and large volumes of wear debris will form in the course of years. Then, the reaction of the organism will frequently be such as to feed as many vessels and reactive tissues as possible to the wear debris region in order to cause foreign matter transporting giant cells to carry away the wear debris particles. As a rule, however, this does not work sufficiently. It is not a rare case that pasty amorphous substances which not only consist of wear debris, but also contain protein and fat constituents, are found in the new joint region after a long time since implantation, on one hand. On the other, thickening occurs in the surrounding vessels. This formation of new vessels and the attempt to carry away the foreign matter particles will then cause a loss of bone structures and a loosening effect.

Revision surgery will then restore a certain stability. A new loosening, however, will occur faster than can be established after the first implantation.

There are also other causes of loosening. Thus, for example, the bone cement serving as an anchoring material was also identified as being a cause of loosening. The result has been that implantations involving no cement are carried out more and more frequently. In doing so, attempts are made to achieve a primary stability which is as high as possible between the prosthetic components and the bone. To this effect, a shape fitting as snugly as possible is aimed at and a trial to obtain it is made by creating a seat which is as good as possible for the components to be anchored. Incorporation of the seat into the bone is mostly made by hand. On the other hand, it is also possible nowadays to design the prosthetic seat in the thigh in a very precise manner by using surgery robots.

Clinical experience has shown that the problems of wear debris formation are also encountered in cementless prosthetic assemblies and can cause the prosthetic components to loosen.

Accordingly, it is the object of the invention to provide a prosthetic hip joint assembly which has a decreased propension to loosen and an increased stability in operation.

BRIEF SUMMARY OF THE INVENTION

The inventive prosthetic hip joint assembly comprises a femoral component with a stem for being anchored in the medullary space of a femur and a head on the distal end of the stem, an acetabular component for being anchored in the pelvic bone with an acetabular cup which pivotedly supports the head of the femoral component, and an articular capsule made of a flexible material, which is located at the femoral component at one end and at the acetabular component at the other end so as to allow the head to move in the acetabular cup and to prevent wear debris from the bearing zone of the head in the acetabular cup from migrating to the outside.

According to the invention, an artificial articular capsule bridges over the femoral component and the acetabular component and, thus, hides the bearing zone in the acetabular cup so that wear debris forming therein cannot exit from the prosthetic hip joint assembly. To this end, for example, the articular capsule may be sealingly connected to an insert of the acetabular cup or to the head and/or to a neck joining the head to the stem. The articular capsule then needs to be of a structure and/or material which permits sufficient movableness of the head which preferably is of a substantially spherical shape, in the acetabular cup. On the other hand, the material and the mounting of the articular capsule requires to be tight enough to prevent microparticles from migrating therethrough. Such microparticles may be a few ms or smaller in size.

The material used for the articular capsule, in particular, is a sheet or foil and/or tissue material. This may be a plastic and/or metallic and/or a natural material. Especially, the materials envisaged are PTFE fibres and/or PETP fibres. It should be particularly advantageous to use Goretex® (a PTFE material available from Gore) or Dacron® (a PETP material available from DuPont (®: a registered trademark). Goretex® has already proved over the recent decades as a material for use in prosthetic vessel assemblies. It is a fibrous material or tissue which may be differing in pore sizes. In addition, it is possible to apply a coating at the inside and/or outside which will cause the pores to largely be sealed. Furthermore, prosthetic vessel assemblies in Dacron® (another fibrous or tissue material) have proved useful, too. Dacron®, as a material for the articular capsule, may also be coated both at its inside and/or outside. In case of need, the articular capsule may consist of a material grown in vitro which has the characteristics of the natural articular capsule tissue.

To allow for a clearance of motion which is as large as possible the articular capsule may be formed as a corrugated bellows. For example, it may have a plurality of concertina-like corrugations. To prevent material ruptures in the region of the corrugations these may have reinforcements.

In addition, the articular capsule may have a bulged-out portion facing away from the bearing zone of the head in the acetabular cup. The bulged-out portion is below the bearing zone in an implanted prosthetic hip joint assembly. It forms a storage volume which is adapted to receive wear debris particles. Furthermore, a body-compatible substance may favourably exist here, which retains these wear debris particles and prevents them from receding back to the joint (fly-catching function).

It is further possible to configure the articular capsule in a way that it has a hose-like extension. Preferably, its end is provided with a closure which is adapted to be opened, e.g. a plug. It is through this plug that the prosthetic hip joint assembly may become accessible by means of a puncture and by advancing a catheter therethrough, and may be rinsed and cleaned, if required.

Especially in the case of complete encapsulation, some sort of lubrication may be effected by body-compatible substances inside the articular capsule so as to keep joint component wear debris as low as possible.

The articular capsule may also be securely fixed to the acetabular component, particularly to an insert of the acetabular cup, in a continuous groove. The articular capsule may be located in this groove by means of a bead and/or a locking collar. It is in the same way that the fixation of the articular capsule may be effected to the femoral component such as the head and/or neck. Also this one may have a continuous groove in which the articular capsule comes to rest with the aid of a bead or by means of a locking collar, in case of need. To prevent the artificial articular capsule from being pulled out of this mount a border projecting beyond the mount may include a bead which prevents the material from being pulled out from beneath the locking collar.

In a very particular, advantageous aspect of the invention, there is a pre-assembled unit comprising an insert, a head, and a capsule fixed to the insert at one end and to the head and/or neck at the other which has a seating cone in the neck. This pre-assembled unit constitutes the joint component proper which is placed in the hip joint area as the last component. After the implantation of the acetabular cup in the pelvis region and the stem in the medullary space of the femur, the encapsulated joint component is inserted in place. At this point, the insert with the articular capsule suspended thereon is introduced into the acetabular cup so as to subsequently position the head with the capsule suspended thereon on the cone of the stem. To make this operation easier, the neck may have a lateral slot through which the cone is inserted. The cone may then be pushed deeper into the seat and, thus, be secured therein.

A special configuration of the articular capsule's outer surface may optimize the bonding behaviour of the woven. There is the assumption that mucous bursae will form and allow an improved movableness of the artificial hip joint with respect to the surrounding tissue. A particularly rough surface, e.g. a fibrous surface, may promote tissue bonding.

In addition, the prosthetic hip joint assembly may have integrated in it an electronic sensor to monitor the function of the prosthetic hip joint assembly. The data measured may be transmitted from inside the human body by means of a telemetering device which can be integrated or may be separately implanted in the prosthetic hip joint assembly. The functions of the joint which require to be monitored include, for example, the intactness of the articular capsule, the heat-up of the joint, and further include pathological motions of the femoral component and the acetabular component inside the bone, etc. This makes it possible to warn the patient of the possible failure or overstress of the prosthetic hip assembly.

BRIEF DESCRIPTION OF THE SEVERAL VIEWS OF THE DRAWINGS

The invention will now be explained in greater detail with reference to the accompanying drawings in which.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Identical elements are designed by the same reference numbers in the following description of various embodiments. The respective description applies to all of the embodiments having the same reference number.

Figure 1:
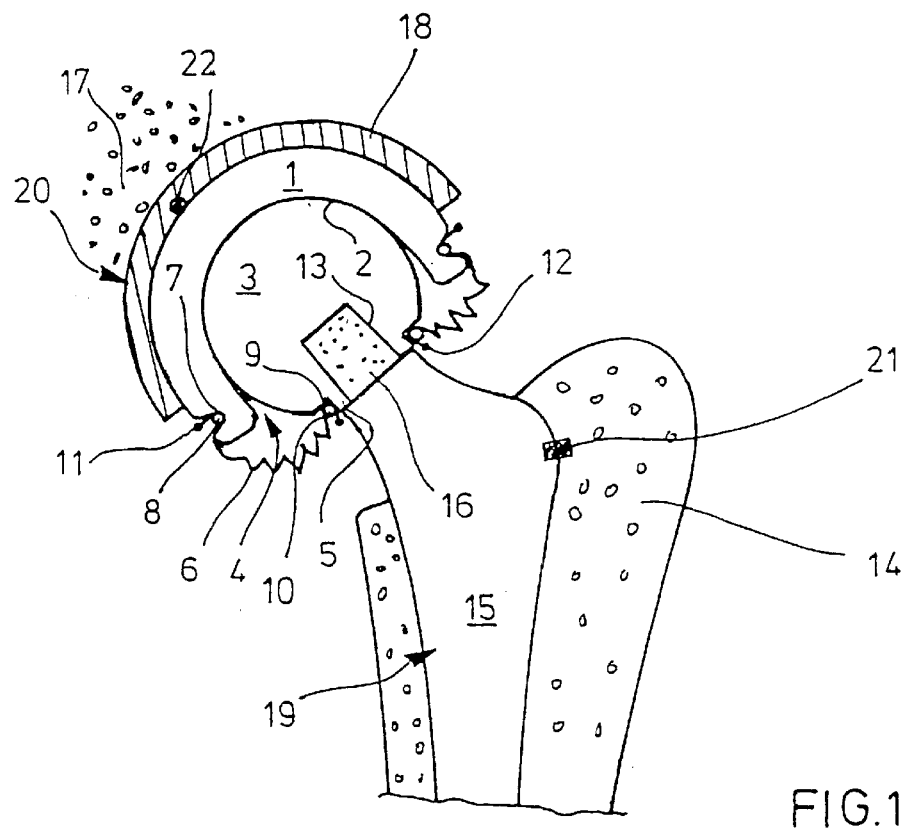
FIG. 1 shows a partial longitudinal section of a prostethic hip joint assembly as implanted in a patient.

Referring to FIG. 1, the prosthetic hip assembly has a cup-shaped insert 1 which can be made of polyethylene, for example. Insert 1 has a ball-cup shaped bearing surface 2 at is inside. Supported in it is a spherically shaped head 3. This one has a projecting cylindrical neck 5 on a portion protruding from an opening 4 of insert 1.

An articular capsule 6 in the form of a corrugated bellows is located at one end in a continuous groove 7 at the outside of insert 1 in the vicinity of opening 4 by means of a locking collar 8. One or more corrugations may be reinforced, as shown in FIG. 1 at reinforcement 29, which is an increase in the wall thickness of articular capsule 6. At the other end, articular capsule 6 is located in a continuous groove 9 in the transition area of head 3 and neck 5 by means of another locking collar 10. At its ends, articular capsule has bead-shaped enlargements 11, 12 which are intended to prevent it from being pulled out of grooves 7, 9.

Ball 3 and neck 4 have a slightly conical seat 13 which is concentric with respect to the neck.

Insert 1, ball 3, and articular capsule 6 constitute a pre-assembled unit. Ball 3 may be secured to insert 1 by snapping it in, if desired.

Implanted in a femur 14 is a stem 15 of the prosthetic hip assembly. It has a projecting cone 16. This one is placed in conical seat 13. Seat 13 and cone 16 define a cone fit securing the mounting of ball 3 on stem 15.

A pelvic bone 17 has implanted in it an acetabular cup 18, which may especially be made of titanium or another metallic material. Pelvic bone 18 may be fixed inside pelvic bone 17 by means of bone screws (not shown). Insert 1 is placed in acetabular cup 18, preferably by forming a snug fit or snap connection.

Ball 3, neck 4, and stem 15 also are jointly designated as a femoral component 19 and acetabular cup 18 and insert 1 also are jointly designated as an acetabular component 20 of the prosthetic hip assembly.

Fixation in the hip joint area is preferably effected in such a way that stem 15 and acetabular cup 18 are initially implanted and the joint unit including components 1, 3, and 6 is placed onto cone 16 and inserted into cup 18.

While in use, wear debris will form when ball 3 moves in insert 1. This debris is confined by articular capsule 6 inside prosthetic hip assembly 1, which avoids loosening the prosthetic assembly and increases its stability in operation. There may be sensors for monitoring the function of the prosthetic assembly such as a sensor 21 between stem 15 and bone 14 or a sensor 22 between acetabular cup 18 and pelvic bone 17. Such sensors 21, 22 are especially used to measure force transfer with the data measured allowing conclusions with respect to overstresses or loosenings.

Figure 2:
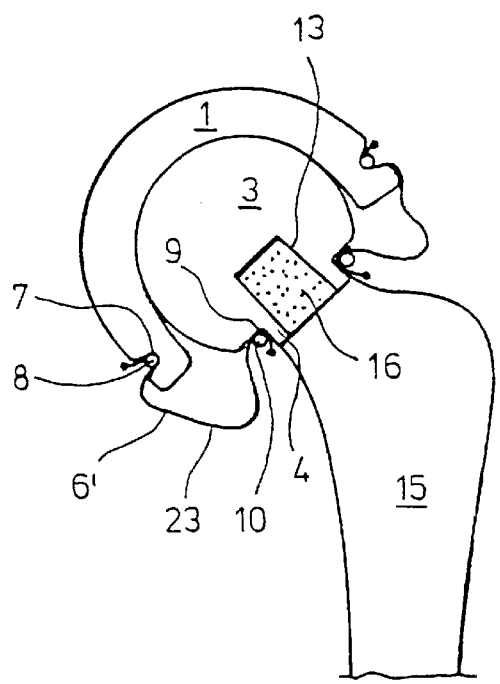
FIG. 2 shows a partial longitudinal section of a second embodiment of the prostethic hip joint assembly.

Referring to FIG. 2, the prosthetic hip assembly has a capsule 6' including a continuous bulged-out portion 23 facing away from head 3. This favours the movableness of head 3 in insert 1, on one hand, and defines a storage volume for wear debris, on the other.

Figure 3:
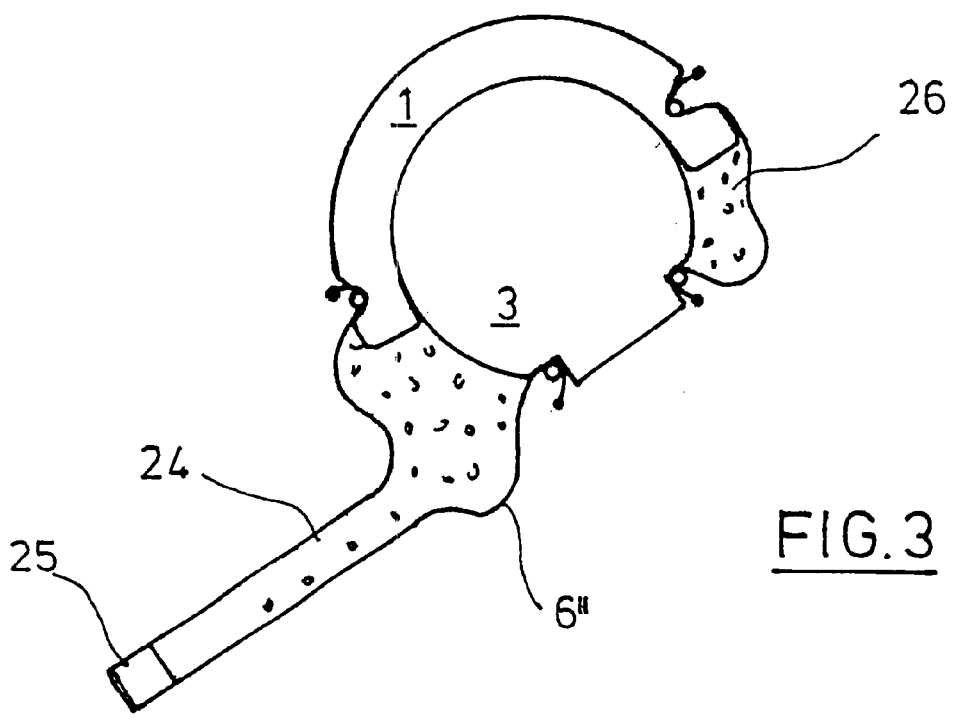
FIG. 3 shows a partial longitudinal section of a third embodiment of the prostethic hip joint assembly.

Referring to FIG. 3, a prosthetic hip joint assembly comprises an articular capsule 5" having a hose-shaped lateral extension 24 which includes a plug-shaped closure 25 which is adapted to be opened. Articular capsule 5" is filled with a bio-compatible lubricant 26 for the prosthetic assembly. The lubricant may be rinsed out or changed via plug 25.

Figure 4:
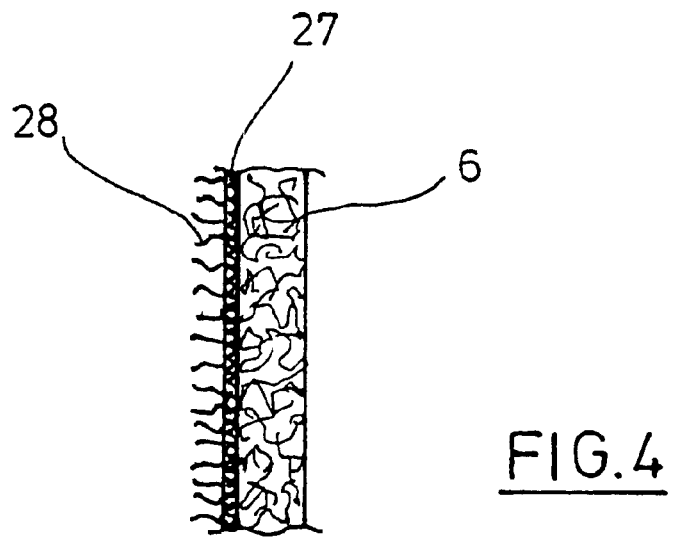
FIG. 4 shows an enlarged section of the articular capsule of the same prostethic hip joint assembly.

Referring to FIG. 4, articular capsule 6 has a wall made of PTFE material (Goretex or the like). Its outside is provided, for example, with a coat 27 which is intended to make the tissue material impermeable to particles. In addition, the material has a roughened surface 28 at its outside which is intended to promote the bonding of tissue material thereto.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An artificial hip joint assembly comprising:
   a femoral component (19) with a stem (15) for being anchored in the medullary space of a femur (14),
   an acetabular component (20) for being anchored in the pelvic bone (17) with an acetabular cup (18),
   a pre-assembled unit comprising an insert which pivotedly supports a ball (3) and which is placed in the acetabular cup (18), the ball (3) having a neck (5, which is connected to the femoral component (19) by a cone connection (13,16), and an articular capsule (6) made of a flexible material, which is securely fixed in a transition area of ball (3) and neck (5) at one end and to the insert at the other end so as to allow the ball (3) to move in the insert and to prevent wear debris from a bearing zone of the ball (3) from migrating to the outside.

2. The prosthetic hip joint assembly according to claim 1 wherein the articular capsule (6) is a corrugated bellows.

3. The prosthetic hip joint assembly according to claim 2 wherein the articular capsule (6) has a reinforcement on at least one corrugation.

4. The prosthetic hip joint assembly according to claim 1 wherein the connection between the articular capsule (6) and the acetabular component (20) and/or the femoral component (19) has a bead (11, 12) and/or a groove (7, 9) and/or a locking collar (8, 10).

5. The prosthetic hip joint assembly according to claim 1 wherein the articular capsule (6") has a hose-like extension (24).

6. The prosthetic hip joint assembly according to claim 1 wherein the articular capsule (6') and/or the extension (24) has a storage volume (23).

7. The prosthetic hip joint assembly according to claim 6 wherein the storage volume exists in a bulged-out portion (23) of the capsule (6').

8. The prosthetic hip joint assembly according to claim 6 wherein the storage volume (23) contains a wear particle retaining substance.

9. The prosthetic hip joint assembly according to claim 1 wherein the articular capsule (6) is made of a sheet or foil and/or tissue material.

10. The prosthetic hip joint assembly according to claim 1 wherein the articular capsule (6) is made of a plastic and/or a metallic and/or a natural material.

11. The prosthetic hip joint assembly according to claim 1 wherein the articular capsule (6) is made of PTFE fibres and/or PETP fibres.

12. The prosthetic hip joint assembly according to claim 1 wherein the articular capsule (6) is made of a material selected from the group consisting of PTFE material or PETP material.

13. The prosthetic hip joint assembly according to claim 1 wherein the articular capsule (6) is made of a partially permeable material which is impermeable to wear debris from the bearing zone of the ball (3) in the acetabular cup (18).

14. The prosthetic hip joint assembly according to claim 13 wherein the articular capsule (6) has applied to it a coat (27) for sealing its pores and/or retaining wear debris.

15. The prosthetic hip joint assembly according to claim 14 wherein the articular capsule (6) has applied to it a material and/or surface finish and/or coat (28) which promotes the bonding of tissue thereto.

16. The prosthetic hip joint assembly according to claim 1 wherein the articular capsule (6) contains a lubricating substance.

17. The prosthetic hip joint assembly according to claim 1 wherein there is at least one electric sensor (21,22) for determining a joint function.

18. The prosthetic hip joint assembly according to claim 17 wherein the sensor (21, 22) is connected to a telemetering device for the transfer of data measured to the surroundings of the human body.

19. An artificial hip joint assembly comprising:

a femoral component (19) with a stem (15) for being anchored in the medullary space of a femur (14), an acetabular component (20) for being anchored in the pelvic bone (17) with an acetabular cup (18), a pre-assembled unit comprising an insert which pivotedly supports a ball (3) and which is placed in the acetabular cup (18), the ball (3) having a neck (4) which is connected to the femoral component (19) by a cone connection (13,16), and an articular capsule (6) made of a flexible material wherein the articular capsule (6) is securely fixed to the ball (3) at one end and to the insert at the other end so as to allow the ball (3) to move in the insert and to prevent wear debris from a bearing zone of the ball (3) from migrating to the outside.

20. An artificial hip joint assembly comprising:

a femoral component (19) with a stem (15) for being anchored in the medullary space of a femur (14), an acetabular component (20) for being anchored in the pelvic bone (17) with an acetabular cup (18), a pre-assembled unit comprising an insert which pivotedly supports a ball (3) and which is placed in the acetabular cup (18), the ball (3) having a neck (5) which is connected to the femoral component (19) by a cone connection (13,16), and an articular capsule (6) made of a flexible material, which is securely fixed to the ball (3) in a transition area at one end and to the insert at the other end so as to allow the ball (3) to move in the insert and to prevent wear debris from a bearing zone of the ball (3) from migrating to the outside.

\* \* \* \* \*